(12) United States Patent
Sybert et al.

(10) Patent No.: US 6,373,519 B1
(45) Date of Patent: Apr. 16, 2002

(54) SYSTEM AND METHOD FOR VISUALLY INSPECTING A CIGARETTE PACKAGING PROCESS

(75) Inventors: Daniel R. Sybert, Midlothian; John D. Hearney, Sutherland; Robert Kucera, Richmond, all of VA (US)

(73) Assignee: Philip Morris Incorporated, New York, NY (US)

( * ) Notice: Subject to any disclaimer, the term of this patent is extended or adjusted under 35 U.S.C. 154(b) by 0 days.

(21) Appl. No.: 09/172,916

(22) Filed: Oct. 15, 1998

(51) Int. Cl.[7] .................................................. H04N 7/18
(52) U.S. Cl. .......................................... 348/86; 348/86
(58) Field of Search .............................. 348/88, 87, 89, 348/90, 86

(56) References Cited

U.S. PATENT DOCUMENTS

| | | | |
|---|---|---|---|
| 4,678,901 A | 7/1987 | Focke et al. ................. 250/223 |
| 4,866,912 A * | 9/1989 | Deutsch ........................ 53/449 |
| 5,101,609 A | 4/1992 | Cook ............................. 53/53 |
| 5,353,356 A | 10/1994 | Waugh et al. |
| 5,366,096 A | 11/1994 | Miller |
| 5,383,322 A | 1/1995 | Collins, Jr. et al. ............. 53/53 |
| 5,412,926 A | 5/1995 | Focke ........................... 53/466 |
| 5,432,600 A | 7/1995 | Grollimund et al. ........ 356/237 |
| 6,054,665 A * | 4/2000 | Focke et al. ................. 209/576 |
| 6,075,882 A * | 6/2000 | Mullins et al. ............. 382/141 |

* cited by examiner

Primary Examiner—Andy Rao
(74) Attorney, Agent, or Firm—Burns, Doane, Swecker & Mathis, LLP (57) ABSTRACT

The present invention provides a system and method for detecting non-conforming cigarette packages during the actual fabrication process. A digital camera is placed in close proximity to the blank feeding and folding turret area of a cigarette packaging machine assembly. Prior to the cigarette package being completely formed, the camera captures a digital image of three sections of the pack blank, namely the dust flaps and the inside front face. The camera is used to visually inspect the pack blank for mis-folded or partially or completely missing dust flaps and a reversed pack blank. The captured image is transferred to a processor which compares the pixel value of the three sections of the pack blank to a predetermined pixel value. If the comparison indicates that the pixel value of any of the three sections does not equal the predetermined pixel value which means that one or more of the dust flaps are either mis-folded or partially/completely missing or that the blank is reversed, the cigarette package is registered as non-conforming. Visually inspecting the blank prior to the cigarette package being completely formed allows for the cigarettes within the non-conforming package to be easily recycled and aids in diagnosing problems in the actual cigarette packaging process.

20 Claims, 7 Drawing Sheets

SYSTEM AND METHOD FOR VISUALLY INSPECTING A CIGARETTE PACKAGING PROCESS

BACKGROUND

The present invention relates generally to cigarette packaging machines and, more particularly, to a system and method for visually inspecting cigarette packages during the fabrication process.

In cigarette manufacturing, quality control has become a matter of increasing attention. Poor packaging (i.e., packaging which does not conform with predetermined quality requirements) detracts from consumer perceptions of the quality of the packaged goods. Perfectly good items are routinely returned for refund and disposal if they are poorly packaged. On-line inspection during manufacture is one way of controlling packaging non-conformities. In an effort to enhance the on-line quality control capabilities of their production machines, many companies have turned to machine vision techniques wherein cameras are used to allow for inspection of the production process.

In the field of cigarette packaging, conventional vision inspection machines focused on inspecting the cigarette packages after the packages have already been formed. In U.S. Pat. No. 5,101,609, issued to Cook, a vision inspection system is disclosed in which a cigarette packaging machine is modified to include an inspection indexing wheel. The inspection indexing wheel is positioned at a post-construction location along the manufacturing process at which the cigarette packages have already been fully constructed. Such systems are wasteful of packaging material and make the recovery of product more difficult. In those instances where a manufacturing machine is repeatedly producing non-conforming packages, these conventional vision inspection systems, such as the one described in Cook, do not assist the manufacturer in identifying where in the fabrication process correction is needed.

There exists a need for a vision inspection system which inspects cigarette packages during the actual fabrication process.

SUMMARY OF THE INVENTION

The present invention seeks to overcome the above-identified deficiencies of the prior art by providing a system and method of detecting non-conforming cigarette packages during the actual fabrication process. According to exemplary embodiments, a digital camera is placed in close proximity to the blank feeding and folding turret area of a cigarette packaging machine assembly. At a location where the cigarette package is partially constructed, the camera captures a digital image of three sections of the pack blank, namely the dust flaps and the inside front panel. The output of the camera is used to visually inspect the pack blank for mis-folded or partially or completely missing dust flaps and a reversed pack blank. The captured image is transferred to a processor which compares the pixel value of the three sections of the pack blank to a predetermined pixel value. If the comparison indicates that the pixel value of any of the three sections does not equal the predetermined pixel value which means that one or more of the dust flaps are either mis-folded or partially/completely missing or that the blank is reversed, the cigarette package is registered as a non-conforming item. Visually inspecting the blank prior to completion of the cigarette package allows for the cigarettes within the non-conforming package to be more easily recycled and aids in diagnosing problems in the actual cigarette packaging process.

BRIEF DESCRIPTION OF THE DRAWINGS

The above objects and features of the present invention will be more apparent from the following description of the preferred embodiments with reference to the accompanying drawings, wherein:

FIG. 3.1 illustrates the inspection areas of an exemplary, conforming pack blank;

FIG. 3.2 illustrates the inspection areas of an exemplary, non-conforming pack blank; and FIGS. 4.1 and 4.2 illustrate exemplary round corner and square corner pack blanks.

DETAILED DESCRIPTION OF THE INVENTION

Toward increasing quality control in a cigarette packaging process, the present invention provides a machine vision inspection system so as to allow for monitoring of the actual process. By placing a camera in close proximity to an area of the cigarette packaging assembly in which a large number of non-conformities commonly occur, non-conforming packages can be readily identified and rejected and the cause of reoccurring non-conformities can be corrected.

Figure 1:
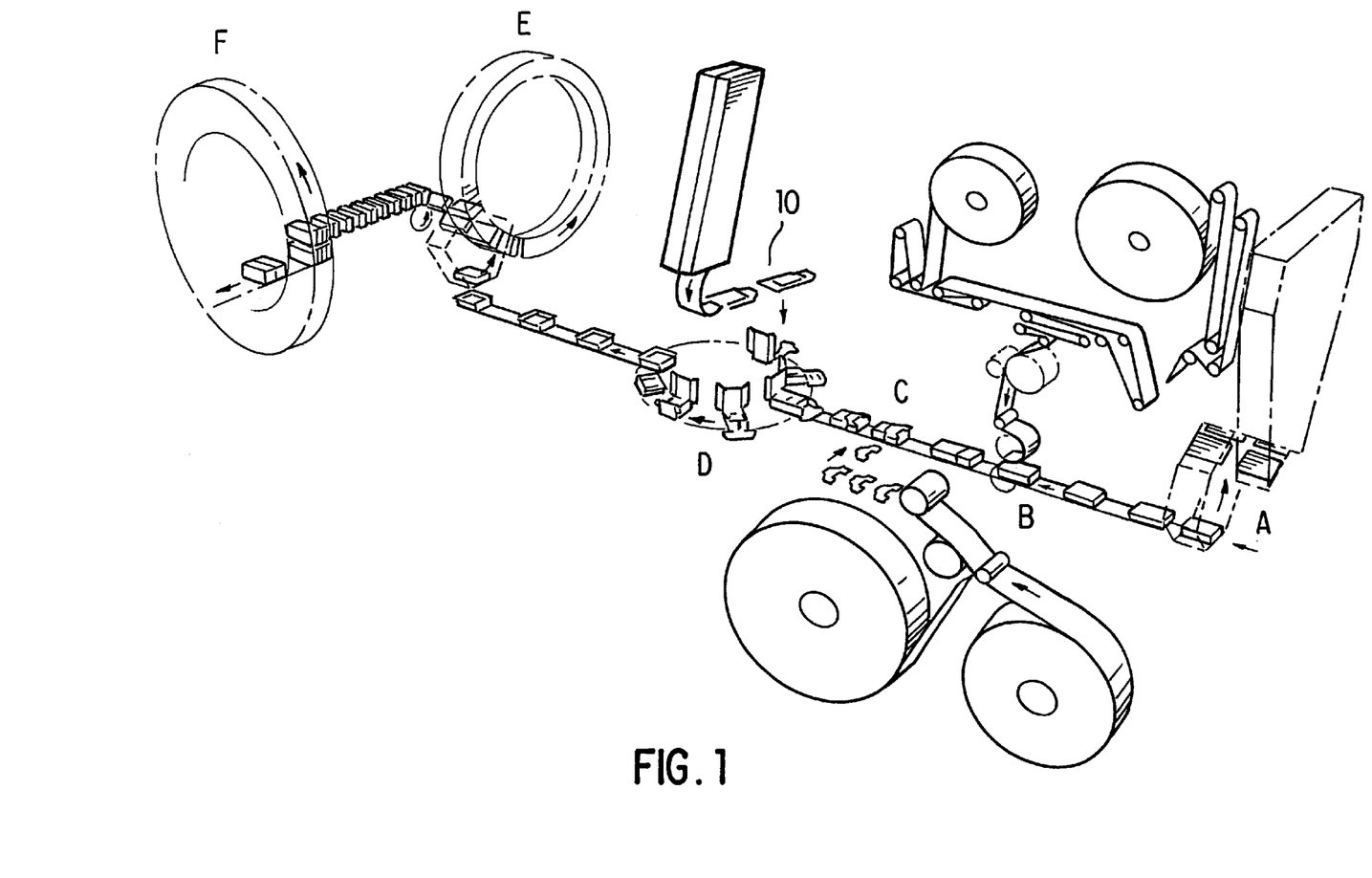
FIG. 1 illustrates an exemplary cigarette packaging process, as implemented in a Focke 350 Round Corner FTB packer, into which the visioninspection technique of the present invention may be employed.

FIG. 1 illustrates an exemplary cigarette packaging process, as implemented in a Focke 350 Round Corner, hinge lid packer, into which the vision inspection technique of the present invention may be employed, among other similarly arranged machines. At stage 1 of the packaging process, a plurality of cigarettes are grouped together so as to form a bundle. Each bundle commonly includes a group of 20 cigarettes. At stage 2, each bundle is then individually wrapped in a foil wrapper. A cardboard insert is placed adjacent to each foil-wrapped bundle at stage 3. The bundles are then routed to a blank feeding and folding turret area (stage 4) where a blank is formed around each of the foil-wrapped bundles to form an individual cigarette package. The cigarette packages are then routed to first and second drying drums (stages 5 and 6, respectively) where the glued packages are allowed to dry prior to being placed in cigarette cartons.

The present invention seeks to identify packaging non-conformities commonly associated with stage 4 (i.e., the blank feeding and folding turret area) of the cigarette packaging process. These non-conformities commonly appear on the cigarette package, which can be either a hard or soft pack cigarette package, as a tear or hole in the back corners of the lid or miter. Such tears or holes are usually the result of the lid dust flaps being partially or completely torn away. One skilled in the art will appreciate that non-conformities can be created in several places in this area of the machine including the blank pre-bending mechanism, the transfer roller assembly prior to glue being applied to the blank, the guides going into the blank plunger, the blank plunger, the dust flap opener, and the transfer of the cigarette bundle to the folding turret.

Many of the settings in this area of the cigarette packaging process are critical and must be precise. These settings are also sensitive to the blank attributes such as flatness, interlocked flaps (multiple blanks), scoring depth, and surface finish. It is in this area of the cigarette packaging process that the vision inspection system of the present invention is implemented.

Figure 2:
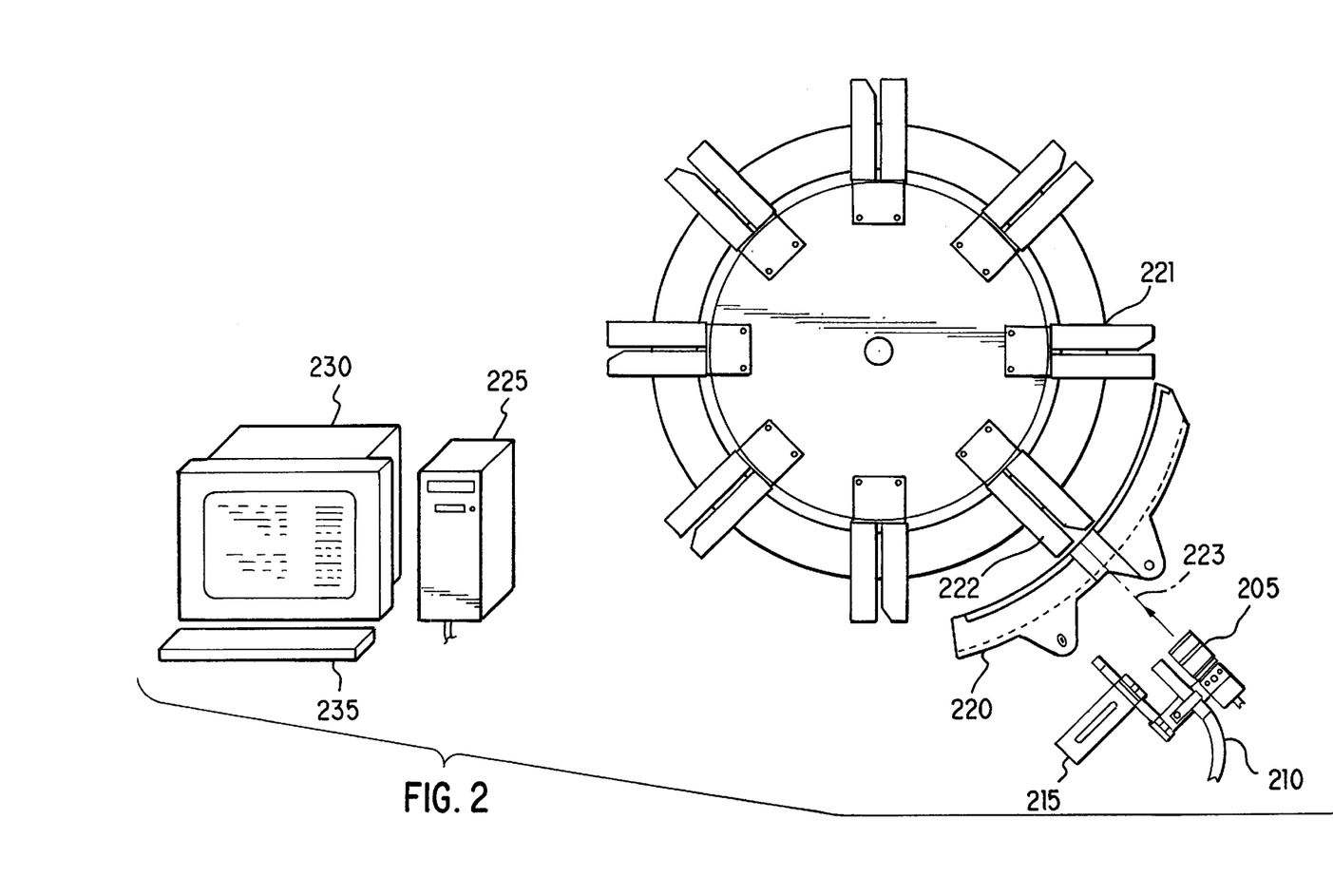
FIG. 2 illustrates the vision inspection system of the present invention as implemented in the exemplary cigarette packaging assembly of FIG. 1.

FIG. 2 illustrates the vision inspection system of the present invention as implemented in the exemplary cigarette packaging assembly of FIG. 1. In FIG. 2, the vision inspection system of the present invention includes a digital camera (preferably a Keyence CV Series 6 mm camera) 205, a lighting device 210, a camera mounting bracket 215, a modified pack guide 220 and a processor 225. Preferably, the digital camera 205 is mounted, via the camera mounting bracket 215, in close proximity to the blank feeding and folding turret area (stage 4) of the cigarette packaging machine assembly. In order to provide the necessary lighting so as to properly illuminate the blank, a lighting device 210, such as a Stocker and Yale fiber optic light source with polarizing cap, is mounted with the camera 205. The camera 205 and lighting device 210 are positioned so as to allow the camera to form electrical signals which, according to a preferred embodiment, represent an image of the blank and the foil-wrapped cigarette bundle during the fabrication process. The pack guide 220, positioned between the camera and the folding turret, is modified to permit a view of the partially constructed pack.

Figure 3:
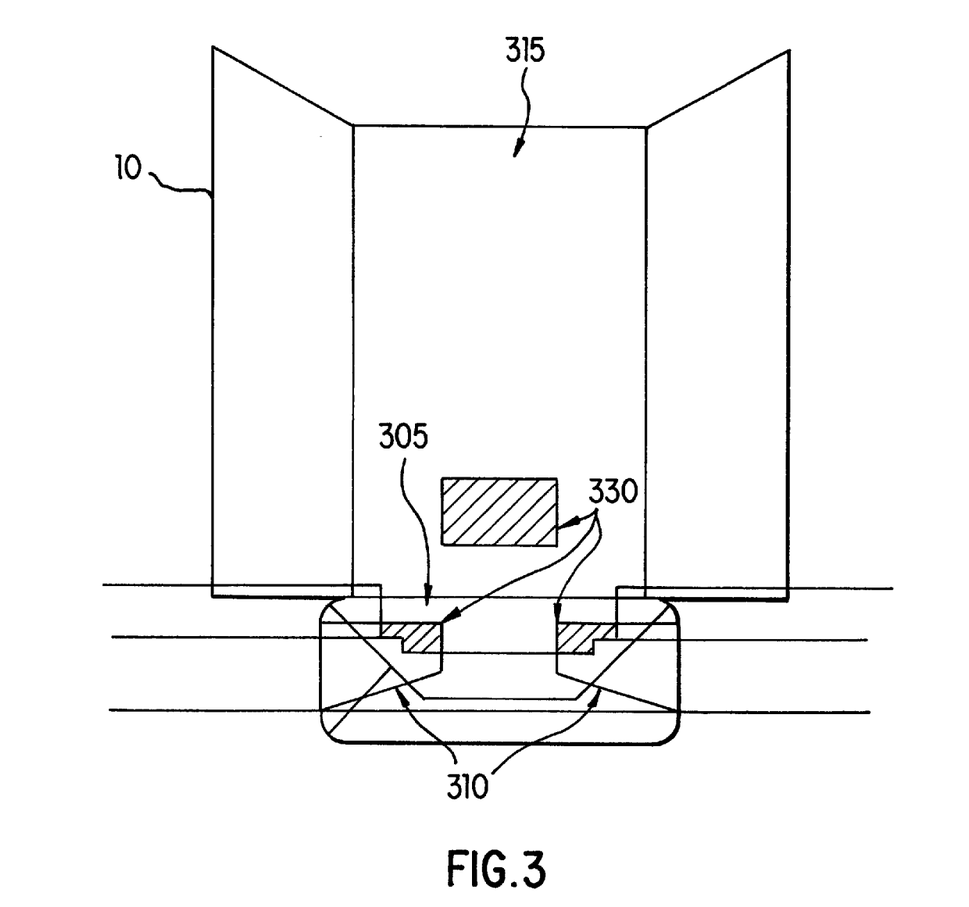
FIG. 3 illustrates an exemplary image captured by the vision inspection system of the present invention.

During the rotation of the folding turret, a switch (not shown) is triggered which signals the digital camera 205 to capture the image of the forming package. FIG. 3 illustrates an exemplary image captured by the digital camera 205. The digital image includes an image of the foil-wrapped bundle 305 and the blank which partially surrounds the bundle. As indicated above, the camera 205 is associated with the proper lighting and polarizers so as to obtain the proper light contrast between the foil and the blank material. This allows the camera to be able to reliably distinguish a non-conformity. According to an embodiment of the present invention, the camera 205 captures a single image of the foil-wrapped bundle and partially surrounding blank and forwards this image (i.e., the formed electrical signals) to the processor 225. One skilled in the art will appreciate that the digital camera could, in the alternative, capture separate images of the sections of the blank which are of greatest interest.

Figure 41:
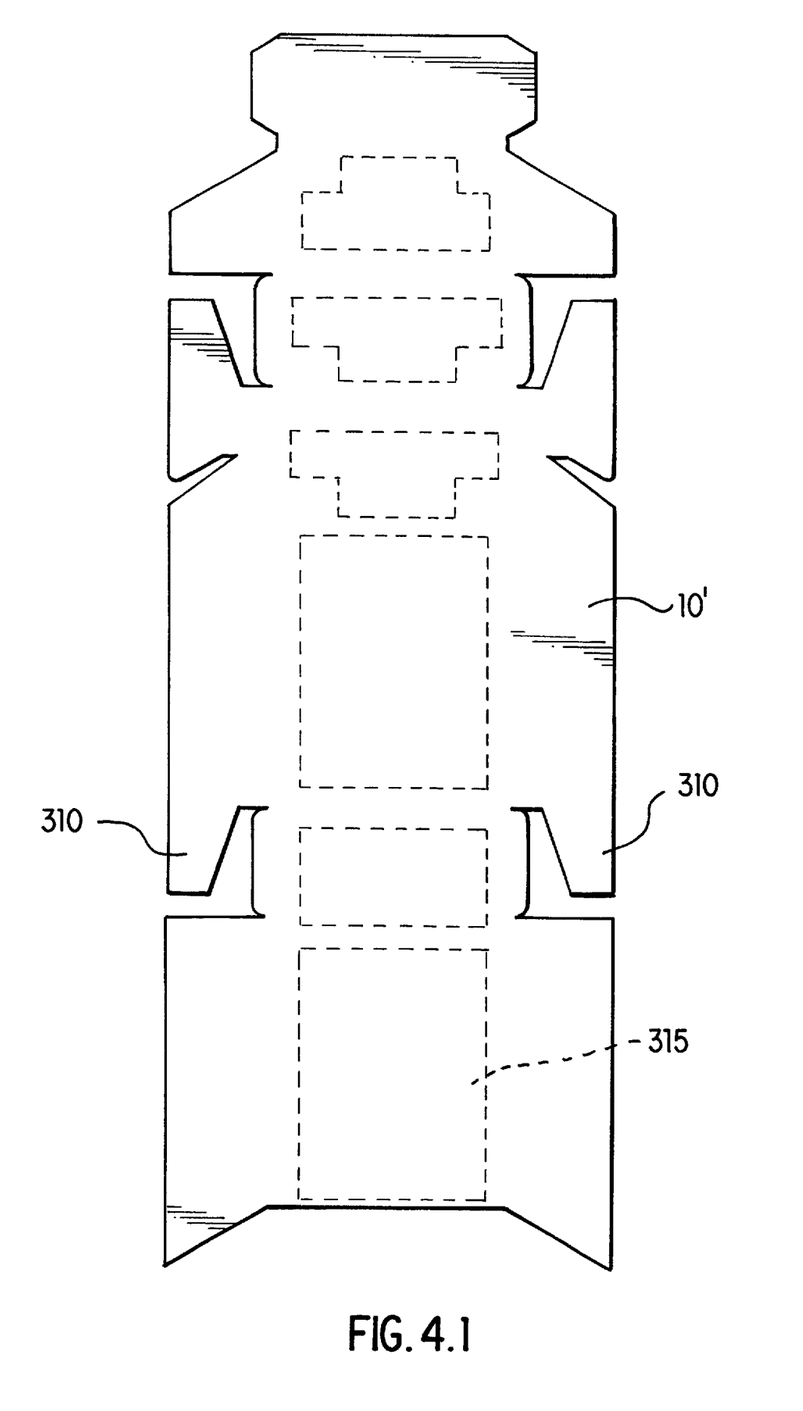
Figure 42:
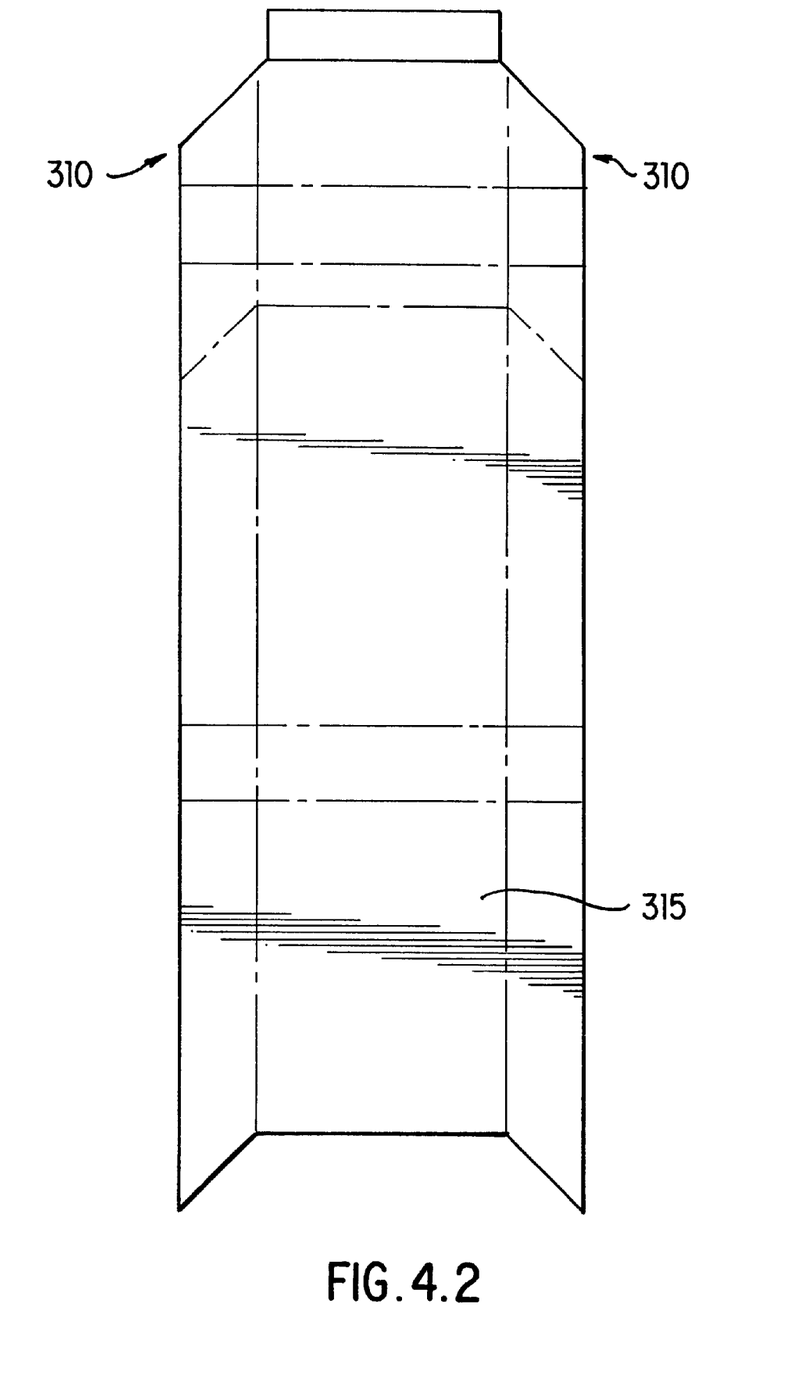

The three areas of the digital image which are of greatest interest to the present invention are the dust flaps 310 and the inside front panel (or face) 315 of the blank. FIG. 4.1 illustrates an exemplary round corner pack blank which may be used in the present invention. In FIG. 4.1, the outside of the pack blank is illustrated. One skilled in the art will appreciate that the other side of the blank (i.e. the inside) is white. FIG. 4.2 illustrates a square corner pack blank which may alternatively be used in the present invention. In FIG. 4.2, the white inside of the pack blank is illustrated. FIGS. 4.1 and 4.2 illustrate the locations of the front panel (or face) and the dust flaps on these exemplary blanks.

When the processor 225 receives the formed electrical signals from the camera, the processor 225 determines, based on these signals, the conformity of the cigarette package. According to the preferred embodiment, the processor 225 receives an image of the foil-wrapped bundle and partially surrounding blank and considers only those sections of the received digital image which represent the objects of interest (i.e., the dust flaps and inside front face). The processor 225 compares the color (i.e., the pixel value) of a section of the digital image of the dust flaps 310 and inside front panel 315 to a predetermined pixel value. In an image of a conforming cigarette package, the color of both the dust flaps 310 and inside front face 315 are white while the surrounding areas appear grey/black.

If the pixel values of the sections of the dust flaps 310 and inside front face 315 equal the predetermined pixel value, the package is registered as conforming and the next package is inspected. If the pixel value of one or both of the sections of the dust flaps 310 does not equal the predetermined pixel value, then this indicates that either one or both of the dust flaps 310 is mis-folded or partially/completely missing. Similarly, if it is determined that the pixel value of the section of the inside front face 315 does not equal the predetermined value, then this indicates that the blank is reversed. When it is determined that either one or more of the dust flaps 310 is mis-folded or partially/completely missing or the blank is reversed, the processor 225 registers the cigarette package as non-conforming. The processor 225 tracks the cigarette packages by tracking the positions thereof via, for example, assigning a number to the individual cigarette packages. In this manner, the processor can simply store a bit with the assigned number of a non-conforming package indicating that it is such. One skilled in the art will appreciate that many other methods of registering a non-conforming package exist which could alternatively be employed.

When a cigarette package is registered as non-conforming, the processor 225 sends a signal to the cigarette packaging machine indicating that the particular cigarette package is to be rejected off the machine. The registered, non-conforming cigarette package is then rejected at the pack reject station which is downstream of the inspection station. The detection and rejection of the cigarette package at this stage of the cigarette assembly process allows for recycling of the cigarette bundle in those instances where only the blank itself is non-conforming (i.e., reversed). Moreover, the information gleaned from the processor comparison aids in diagnosing problems with the cigarette packaging machine. For example, a repeated indication that the blank is reversed could indicate that a group of blanks were incorrectly inserted in the feeding hopper. In such an event, the operator could stop the packaging operation and correct the error, thereby circumventing the continued application of the incorrectly inserted blanks to the wrapped bundles of cigarettes.

To further aid in the diagnosis process, a computer monitor 230 and data input device 235, such as a keyboard, are associated with the processor 225 thereby allowing for the display and manipulation of information. Such information could include, for example, the day and time in which non-conformities were detected, the number of non-conformities encountered over a given period of time, the types of non-conformities encountered during specific periods of time, etc. This information would allow the machine operator to quickly identify and remedy problems with the manufacturing process that conventional post-fabrication inspection systems cannot.

Figure 31:
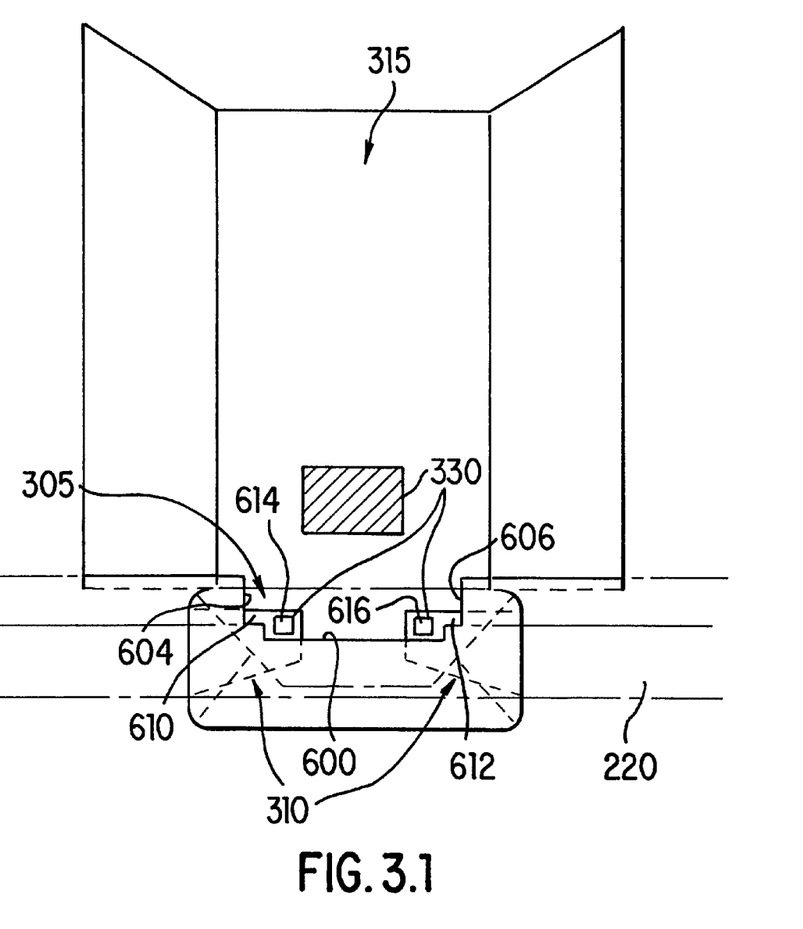
Figure 32:
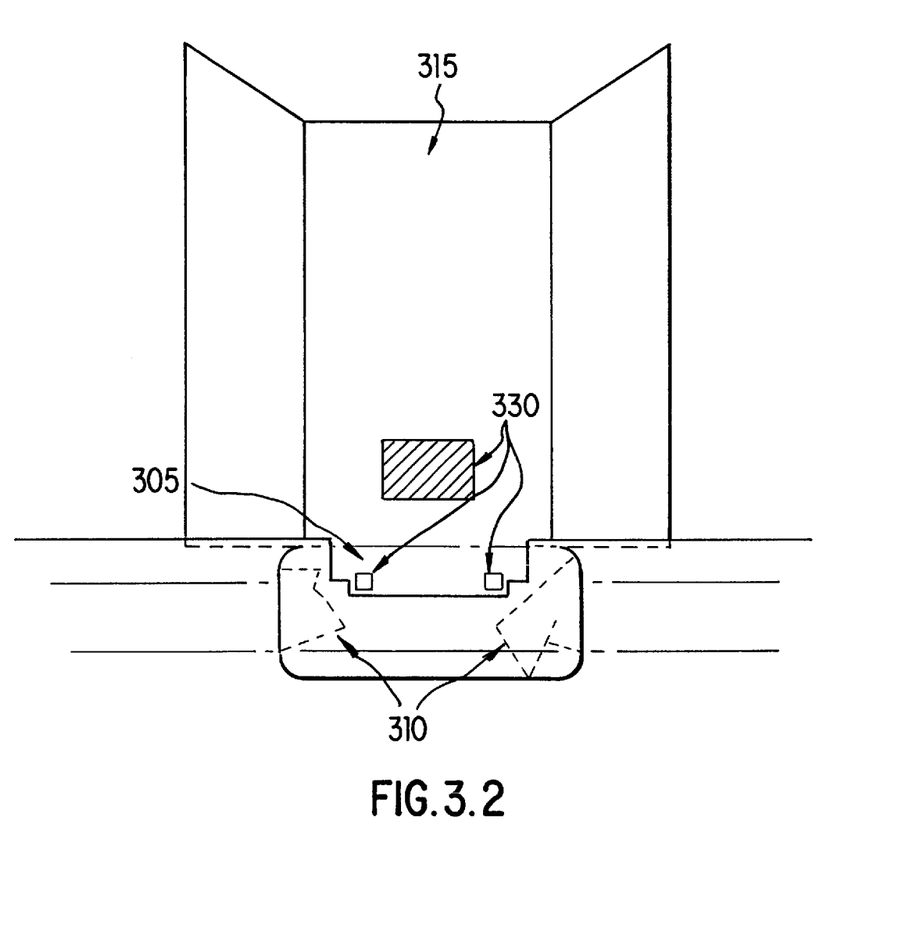

Referring now to FIG. 3.1, preferably the guide rail 220 includes a viewing port or notch 600 having right and left edge portions 604, 606 which expose only end portions 610, 612 of the dust flaps 310 to view by the video camera 205. Preferably, the inspection areas are limited in regions 614, 616 of the end portions 610, 612, such that if a dust flap is missing or poorly folded, such as shown in FIG. 3.2, the dust flap is hidden from view behind the guide 220 and/or displaced sufficiently to affect the pixel values to a cognizable degree in the inspection areas 614, 616. With such an arrangement, sensitivity to dust flap non-conformities is increased.

Advantageously, the viewing port 600 is configured such that the retaining action of the guide 220 upon the folded dust flaps 310 is not interrupted at the inspection station. Accordingly, the partially folded cigarette package is retained in its folded condition as it is moved past the viewing port 600.

Rejection of the detected non-conforming packages may be undertaken downstream of the folding turret so as to avoid the execution of additional packaging steps such as the application of cellophane and tear strips. As a result, waste of materials is avoided.

The foregoing has described the principles, preferred embodiments and modes of operation of the present invention. However, the invention should not be construed as being limited to the particular embodiments discussed above. For example, one skilled in the art will appreciate that the implementation of the vision inspection system of the present invention in a Focke 350 Round Corner, hinge lid packer in the above-described embodiments is merely exemplary and that the present invention is equally applicable to other types of cigarette packaging machines. Moreover, one skilled in the art will appreciate that the present invention is not only applicable to cigarette packaging systems, but is equally applicable to other types of systems where quality is desired in the packaging fabrication process. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A system for inspecting cigarette packages, each package having a pack blank comprising a plurality of dust flaps and an inside front face, in a cigarette packaging machine, said system comprising:
    a camera for forming, prior to a cigarette package being formed, electrical signals representing an image of the dust flaps and the inside front face of the cigarette package and for outputting the electrical signals;
    a guide for maintaining said dust flaps in a folded condition as said cigarette package is moved along a portion of said guide, said guide portion configured to partially expose said folded dust flaps to said camera; and
    a processor for receiving the electrical signals from the camera and determining based thereon a conformity of the cigarette package.

2. The system of claim 1 wherein the processor compares an image of a section of each dust flap and a section of the inside front face to a predetermined image.

3. The system of claim 2 wherein the comparison is a pixel color comparison.

4. The system of claim 1 wherein the processor determines, by comparing the image to a predetermined image, if one or more of the dust flaps is mis-folded or partially/completely missing and if the pack blank is reversed.

5. The system of claim 1 wherein the registering of the cigarette package is a transparent registering.

6. The system of claim 1 further comprising a lighting device, located in proximity to the camera, for illuminating the dust flaps and inside front face.

7. The system of claim 1 further comprising a monitor for displaying diagnostic information.

8. A method of inspecting cigarette packages, each package having a pack blank comprising a plurality of dust flaps and an inside front face, in a cigarette packaging machine, the method comprising the steps of:
    retaining folded dust flaps of a cigarette package while bringing portions of said dust flaps into view of a camera;
    forming, prior to said cigarette package being completely formed, electrical signals representing an image of the dust flap portions and the inside front face of the cigarette package;
    comparing the image to a predetermined image; and
    registering, when the comparison determines that the image and the predetermined image are different, the cigarette package as non-conforming.

9. The method of claim 8 wherein the comparing step further comprises the step of comparing a section of each dust flap and a section of the inside front face to the predetermined image.

10. The method of claim 9 wherein the comparing step further comprises the step of:
    comparing a pixel value of each section to a predetermined value.

11. The method of claim 8 wherein the step of registering is a transparent registering of the cigarette package.

12. The method of claim 8 wherein the comparison step determines whether one or more of the dust flaps is misfolded or partially/completely missing and whether the blank is reversed.

13. The method of claim 8 further comprising the step of:
    displaying diagnostic information.

14. A system for manufacturing cigarette packages, each cigarette package having a pack blank comprising dust flaps and an inside front face, the system comprising:
    a cigarette packaging machine comprising a folding turret;
    a guide for maintaining dust flaps of a cigarette package in a folded condition as said cigarette package is moved along a portion of said guide, said guide portion configured to partially expose said folded dust flaps;
    a camera, positioned in proximity to the folding turret and said guide, for capturing an image of one or more sections of the pack blank prior to the cigarette package being completely formed and for outputting the image; and
    a processor for receiving the image, comparing a pixel value of each of the one or more sections to a predetermined value and registering, when the comparison indicates that at least one of the pixel values is different than the predetermined value, the cigarette package as non-conforming.

15. The system of claim 14 wherein the one or more sections of the pack blank are sections of the dust flaps and the inside front face.

16. The system of claim 15 wherein the processor determines, by making the comparison, whether one or more of the dust flaps is mis-folded or partially/completely missing and whether the pack blank is reversed.

17. The system of claim 14 further comprising a monitor for displaying diagnostic information.

18. A method for manufacturing cigarette packages, each cigarette package having a pack blank comprising dust flaps and an inside front face, the method comprising the steps of:
    folding, via a folding turret, a pack blank around a bundle of cigarettes;

retaining said folded blank while bringing portions of said blank into view of a camera;

capturing, during the retaining step, an image of at least one section of the pack blank;

comparing a pixel value of the at least one section to a predetermined value; and registering, when the comparing step indicates that the pixel value is different than the predetermined value, the cigarette package as non-conforming.

19. The method of claim 18 wherein the at least one section of the pack blank includes sections of the dust flaps and the inside front face.

20. The method of claim 19 wherein the comparing step determines whether one or more of the dust flaps is misfolded or partially/completely missing and whether the pack blank is reversed.

* * * * *